United States Patent
Zhao et al.

(10) Patent No.: US 11,370,836 B2
(45) Date of Patent: Jun. 28, 2022

(54) MONOCLONAL ANTIBODY BINDING TO HUMAN IL-5, PREPARATION METHOD THEREFOR AND USE THEREOF

(71) Applicant: SUNSHINE GUOJIAN PHARMACEUTICAL (SHANGHAI) CO., LTD., Shanghai (CN)

(72) Inventors: Jie Zhao, Shanghai (CN); Haomin Huang, Shanghai (CN); Zhenping Zhu, Shanghai (CN); Liangfeng Jiang, Shanghai (CN)

(73) Assignee: SUNSHINE GUOJIAN PHARMACEUTICAL (SHANGHAI) CO., LTD., Shanghai (CN)

( * ) Notice: Subject to any disclaimer, the term of this patent is extended or adjusted under 35 U.S.C. 154(b) by 136 days.

(21) Appl. No.: 16/956,456

(22) PCT Filed: Nov. 30, 2018

(86) PCT No.: PCT/CN2018/118534
§ 371 (c)(1),
(2) Date: Jun. 19, 2020

(87) PCT Pub. No.: WO2019/120060
PCT Pub. Date: Jun. 27, 2019

(65) Prior Publication Data
US 2021/0171621 A1    Jun. 10, 2021

(30) Foreign Application Priority Data
Dec. 21, 2017  (CN) .......................... 201711393147.1

(51) Int. Cl.
| | | |
|---|---|---|
| *C07K 16/24* | (2006.01) |
| *C12N 5/10* | (2006.01) |
| *A61K 39/395* | (2006.01) |
| *C12N 15/63* | (2006.01) |
| *G01N 33/53* | (2006.01) |
| *A61K 39/00* | (2006.01) |

(52) U.S. Cl.
CPC .......... *C07K 16/244* (2013.01); *A61K 39/395* (2013.01); *C12N 15/63* (2013.01); *A61K 2039/505* (2013.01); *C07K 2317/24* (2013.01); *C07K 2317/565* (2013.01)

(58) Field of Classification Search
None
See application file for complete search history.

(56) References Cited

FOREIGN PATENT DOCUMENTS

| CN | 1189190 A | 7/1998 |
|---|---|---|
| CN | 1656122 A | 8/2005 |
| CN | 101848732 A | 9/2010 |
| PT | 1527100 E | 5/2005 |
| WO | 2010136483 A2 | 12/2010 |

OTHER PUBLICATIONS

Hilvering et al, (Therapeutic Advances in Respiratory Disease, 2015, vol. 9(4), pp. 135-145).*
Castro et al, (American Journal of Respiratory and Critical Care Medicine, 2011, vol. 184, pp. 1125-1132).*
Molfino et al, (Clinical & Experimental Allergy, 2011, vol. 42, pp. 712-737).*
International Search Report and Written Opinion for PCT/CN2018/118534, dated Mar. 1, 2019.

* cited by examiner

*Primary Examiner* — Bridget E Bunner
*Assistant Examiner* — Fozia M Hamud
(74) *Attorney, Agent, or Firm* — Greer, Burns & Crain, Ltd.; Gregory P. Einhorn

(57) ABSTRACT

Disclosed is a monoclonal antibody that binds to human IL-5. The monoclonal antibody that binds to human IL-5 has a good biological activity for inhibiting TF-1 cell proliferation induced by IL-5 and blocking the interaction between IL-5 and IL-5RA, has a different antigen epitope from the known anti-human IL-5 antibody, can be used for preparing drugs for treating diseases mediated by the over-expression of eosinophilic granulocytes (such as asthma), and has a good clinical application prospect.

19 Claims, 4 Drawing Sheets
Specification includes a Sequence Listing.

| | Nucala | Hu39D10 | 4-6 Humanized |
|---|---|---|---|
| Human wild IL-5 (Control) | | | |
| 85K | | | |
| 86C | 0.0967 | 0.1391 | 0.0954 |
| 87G | | | |
| 88E | | | |
| 89E | | | |
| 90R | | 0.4087 | |
| 91R | | 0.1797 | 0.0844 |
| 92R | | | |
| 93V | | | |
| 94N | | | |
| 95Q | | | |
| 96F | 0.1903 | 0.4539 | 0.3469 |
| 97L | | | |
| 98D | | | |
| 99Y | | | |
| 100L | | | |
| 101Q | | | |
| 102E | | | |
| 103F | | | |
| 104L | 0.1091 | 0.1102 | 0.1238 |
| 109T | | | |
| 110E | | | |
| 111W | | | |

MONOCLONAL ANTIBODY BINDING TO HUMAN IL-5, PREPARATION METHOD THEREFOR AND USE THEREOF

RELATED APPLICATIONS

This application is a national phase application claiming benefit of priority under 35 U.S.C. § 371 to International (PCT) Patent Application serial number PCT/CN2018/118534, filed Nov. 30, 2018, which claims benefit of priority to Chinese Application 201711393147.1, filed Dec. 21, 2017. The aforementioned applications are expressly incorporated herein by reference in their entirety and for all purposes.

FIELD OF THE INVENTION

The present invention relates to the field of antibodies. More specifically, the present invention discloses a monoclonal antibody that binds to human IL-5, its preparation method and use.

BACKGROUND OF THE INVENTION

Bronchial asthma (asthma for short) is a kind of respiratory system disease characterized by chronic airway inflammation, which is involved by various inflammatory cells such as mast cells and eosinophils (EO), and immune cells such as T lymphocytes. It is mainly manifested by the accumulation of bronchial secretions and inflammatory responses such as infiltration of lymphocytes, macrophages and eosinophils. Patients with asthma often show airway hyperresponsiveness and reversible airflow limitation, such as repeated wheezing, chest tightness, or cough, and severe cases may be accompanied by symptoms of dyspnea, and further non-specific bronchial allergies caused by airway obstruction (though reversible).

In recent years, the prevalence and mortality rate of asthma showed rising trend. According to statistics, about 300 million people around the world suffer from asthma, and it is estimated there are about 30 million asthma patients in China. At present, the basic method of clinical treatment of asthma is to use anti-inflammatory treatment, including inhaled glucocorticoids, β2 receptor agonists, leukotriene-regulators, anticholinergic drugs, phosphodiesterase inhibitors, theophylline drugs, antihistamines and other antiallergic drugs. However, it is still not efficient for the control of symptoms in severe asthma patients, and even systemic glucocorticoid therapy is required, which may cause systemic side effects such as osteoporosis, infection and growth restriction. Therefore, exploring new targets for asthma treatment, reducing acute attacks of hormone-insensitive asthma patients, improving asthma symptoms, alleviating lung function, and improving the quality of life of asthma patients have become new strategies for clinical asthma treatment.

Eosinophils are thought to play a critical role in many diseases caused by inflammation including asthma. Among them, eosinophils play a key role in triggering the accumulation of secretions. The number of activated eosinophils is greatly increased in the blood, bronchial secretions, and lung glandular cell tissues of patients with chronic asthma, and is proportional to the severity of the disease. During the treatment with steroid drugs, it was found that the remission of the disease is associated with a decrease in the number of eosinophils.

Interleukin-5 (IL-5) is a glycosylated protein cytokine that can form homodimers and is mainly produced by activated CD4+ T lymphocytes. In the human body, the growth and differentiation of eosinophils are mainly accomplished by the interaction of IL-5 with IL-5 receptor on the cell surface. IL-5 has two receptor subunits, alpha (RA) and beta (RB). IL-5 first binds to IL-5RA, but this interaction cannot mediate signal transduction. IL-5 binds to IL-5RA, and then binds to IL-5RB, which will increase the affinity of IL-5 and its receptor complex and initiate signal transduction. Both IL-5RA and IL-5RB subunits are necessary for signal transduction. In animal models, the number of eosinophils in the peripheral blood and tissues of IL-5 transgenic mice is greatly increased in the absence of antigen stimulation. In studies using mouse and monkey models of allergic asthma, injection of anti-IL-5 monoclonal antibodies into the animals can effectively inhibit the penetration of eosinophils into the respiratory tract and can suppress the development of bronchial allergic reactions (refer to: Hart T K. Cook R M, Ziaamirhosseini P et al. Preclinical efficacy and safety of mepolizumab (SB-240563), a humanized monoclonal antibody to IL-5, in cynomolgus monkeys[J]. The Journal of Allergy and Clinical Immunology, 2001, 108(2): 250-257; Egan R W, Athwal D, Bodmer M W et al. Effect of Sch 55700, a humanized monoclonal antibody to human interleukin-5, on eosinophilic responses and bronchial hyperreactivity[J]. Arzneimittelforschung, 1999, 49(09): 779-790). Clinically, the response and efficacy of patients with severe hypereosinophilia asthma to medication are positively correlated with the number of eosinophils in their peripheral blood: the higher the number of eosinophils, the better the efficacy. Foreign clinical trials of similar drugs show that when asthma exacerbation rate is used as the main indicator, compared with the control group, anti-IL-5 monoclonal antibody drugs can reduce the exacerbation rate by more than 50%, as well as improve lung function and reduce the dosage of glucocorticoids and improve the quality of life of asthma patients (refer to: Ortega H, Liu M C, Pavord I D, et al. Mepolizumab Treatment in Patients with Severe Eosinophilic Asthma[J]. The New England Journal of Medicine, 2014, 371(13): 1198-1207; Bjermer L, Lemiere C, Maspero J F et al. Reslizumab for Inadequately Controlled Asthma With Elevated Blood Eosinophil Levels: A Randomized Phase 3 Study[J]. Chest, 2016, 150(4): 789-798).

Currently, GSK's Mepolizumab and TEVA's Reslizumab have been approved by the FDA for the treatment of severe hypereosinophilic asthma. However, there is still an urgent need to develop new, specific, and highly effective drugs targeting IL-5 to fill the gaps in the market for similar drugs, so as to improve the quality of life of asthma patients and benefit them.

SUMMARY OF THE INVENTION

In order to solve the above technical problems, the inventors of the present invention conducted a large number of experiments, from antigen immunization, hybridoma screening, antibody expression purification until biological activity identification, and finally obtained an anti-human IL-5 antibody having a completely new CDR sequence. Compared with the known anti-human IL-5 antibodies, the present antibody has higher biological activities on inhibition of IL-5 dependent cell proliferation as well as blocking of IL-5 and its receptor L-5RA. Furthermore, it can be seen from the analysis of antigen binding epitopes that the anti-human IL-5 antibody of the present invention has a different epitope binding site from the known anti-human IL-5 antibodies.

In order to achieve the above objects, the present invention adopts the following technical solutions:

The first aspect of the present invention provides a monoclonal antibody that binds to human IL-5. When binding to human IL-5, the monoclonal antibody binds to at least one of the following residues: 86C, 91R, 96F or 104L of SEQ ID NO: 1, and the monoclonal antibody can block the binding of IL-5 and IL-5RA.

Preferably, when binding to human IL-5, the monoclonal antibody binds at least two of the following residues: 86C, 91R, 96F, or 104L of SEQ ID NO: 1.

More preferably, when binding to human IL-5, the monoclonal antibody binds at least three of the following residues: 86C, 91R, 96F, or 104L of SEQ ID NO: 1.

Most preferably, when binding to human IL-5, the monoclonal antibody only binds the following four residues: 86C, 91R, 96F and 104L of SEQ ID NO: 1.

The second aspect of the present invention provides a monoclonal antibody that binds to human IL-5. The monoclonal antibody that binds to human IL-5 comprises: (a) a heavy chain, the heavy chain comprising heavy chain complementarity determining regions H-CDR1, H-CDR2, H-CDR3, the H-CDR1 having an amino acid sequence as shown in SEQ ID NO: 6, the H-CDR2 having an amino acid sequence as shown in SEQ ID NO: 7, the H-CDR3 having an amino acid sequence as shown in SEQ ID NO: 8, and (b) a light chain, the light chain comprising light chain complementarity determining regions L-CDR1, L-CDR2, L-CDR3, the L-CDR1 having an amino acid sequence as shown in SEQ ID NO: 9, the L-CDR2 having an amino acid sequence as shown in SEQ ID NO: 10, and the L-CDR3 having an amino acid sequence as shown in SEQ ID NO: 11.

Preferably, the monoclonal antibody that binds to human IL-5 is a murine antibody, a chimeric antibody or a humanized antibody.

More preferably, the heavy chain of the monoclonal antibody that binds to human IL-5 comprises a heavy chain variable region having an amino acid sequence as shown in SEQ ID NO: 3, and the light chain comprises a light chain variable region having an amino acid sequence as shown in SEQ ID NO: 5.

More preferably, the heavy chain variable region of the monoclonal antibody that binds to human IL-5 has an amino acid sequence as shown in SEQ ID NO: 13, and the light chain variable region has an amino acid sequence as shown in SEQ ID NO: 15.

Preferably, the heavy chain of the monoclonal antibody that binds to human IL-5 has an amino acid sequence as shown in SEQ ID NO: 16, and the light chain has an amino acid sequence as shown in SEQ ID NO: 17.

The third aspect of the present invention provides an isolated nucleotide molecule, which encodes the monoclonal antibody that binds to human IL-5 as described above.

Preferably, the nucleotide molecule has a nucleotide sequence encoding the heavy chain variable region as shown in SEQ ID NO: 2, and a nucleotide sequence encoding the light chain variable region as shown in SEQ ID NO: 4.

Preferably, the nucleotide molecule has a nucleotide sequence encoding the heavy chain variable region as shown in SEQ ID NO: 12, and a nucleotide sequence encoding the light chain variable region as shown in SEQ ID NO: 14.

The fourth aspect of the present invention provides an expression vector, which comprises the nucleotide molecule as described above.

The fifth aspect of the present invention provides a host cell, which comprises the expression vector as described above.

The sixth aspect of the present invention provides a method for preparing the monoclonal antibody that binds to human IL-5 as described above, which comprises the following steps: (a) cultivating the host cell as described above under expression conditions, thereby expressing the monoclonal antibody that binds to human IL-5: (b) isolating and purifying the monoclonal antibody that binds to human IL-5 of step (a).

The seventh aspect of the present invention provides a pharmaceutical composition, which comprises the monoclonal antibody that binds to human IL-5 as described above and a pharmaceutically acceptable carrier.

The eighth aspect of the present invention provides use of the monoclonal antibody that binds to human IL-5 as described above or the pharmaceutical composition as described above for the preparation of a medicament for treatment of diseases mediated by eosinophil overexpression.

Preferably, the diseases mediated by eosinophil overexpression include asthma, granulomatosis with polyangiitis, chronic obstructive pulmonary disease, nasal polyps, allergic dermatitis, hypereosinophilia syndrome, etc. and more preferably, the disease mediated by eosinophil overexpression is asthma.

Beneficial Effect:

The anti-human IL-5 monoclonal antibody selected by the present invention can specifically bind to human IL-5, and compared with known anti-human IL-5 antibodies, has better biological activities on inhibiting IL-5-induced TF-1 cell proliferation and blocking the interaction between IL-5 and IL-5RA. And it has a different antigen epitope from the known anti-human IL-5 antibodies, can be used for the preparation of a madicament for treatment of diseases mediated by eosinophil overexpression (such as asthma), possessing a good clinical application prospect.

DETAILED DESCRIPTION OF THE INVENTION

Figure 1:
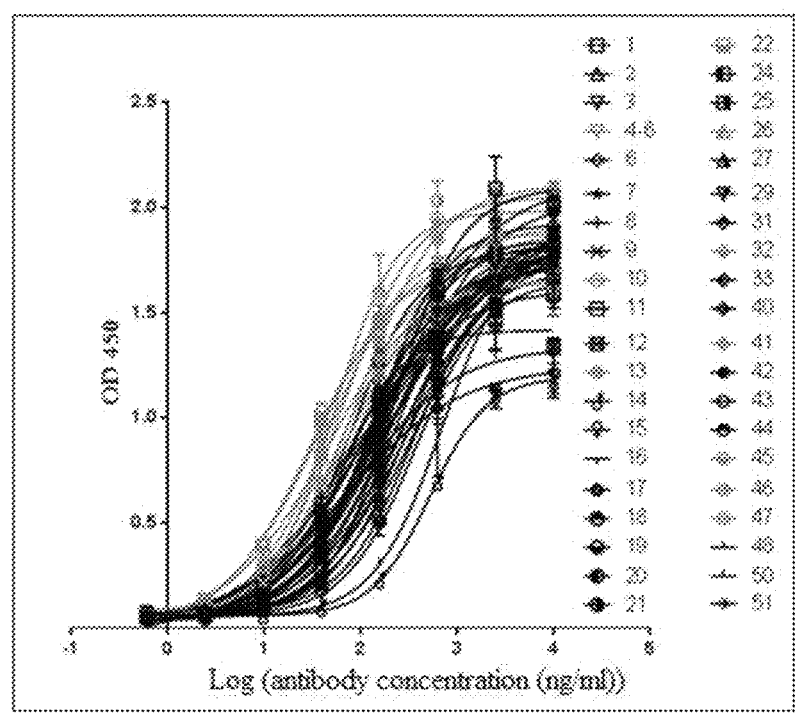
FIG. 1 is a graph showing the determination results of the relative affinity of murine anti-human IL-5 monoclonal antibody against IL-5 antigen.
Figure 2:
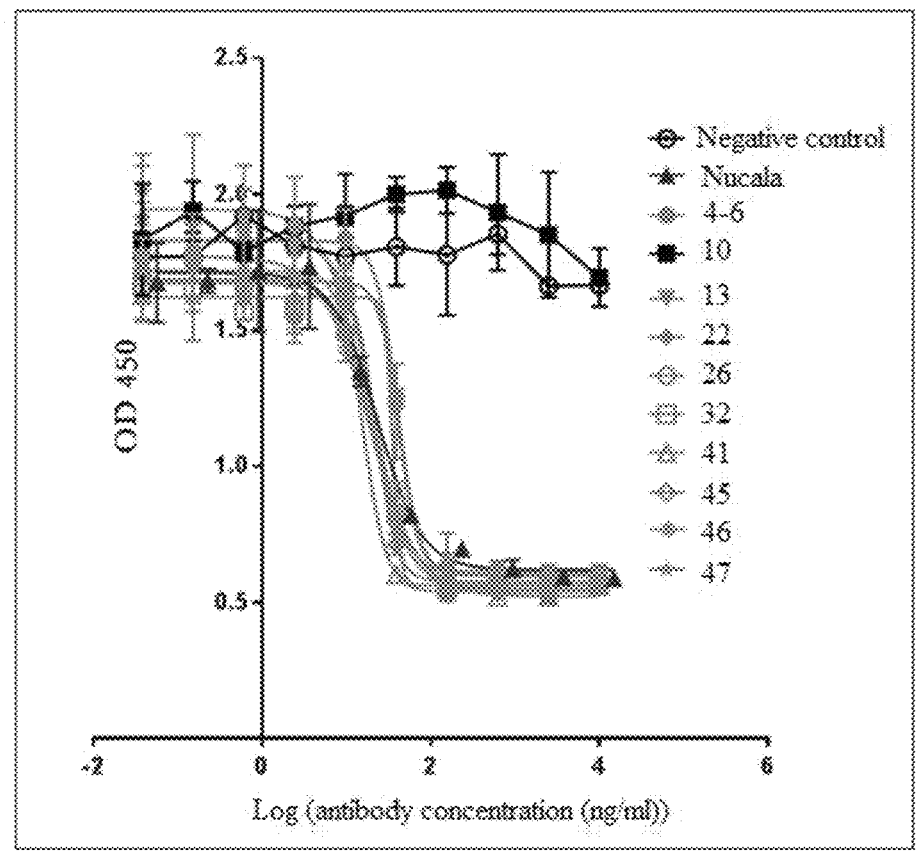
FIG. 2 is a graph showing the determination results of the inhibitory effect of murine anti-human IL-5 monoclonal antibody on IL-5-induced TF-1 cell proliferation.

In the present invention, the term "monoclonal antibody (mAb)" refers to an antibody obtained from a population of substantially homogeneous antibodies, that is, the individual antibodies contained in the population are the same, except for a few possible naturally occurring mutations. Monoclonal antibodies target a single antigen site with high specificity. Moreover, unlike conventional polyclonal antibody preparations (usually with different antibodies directed against different determinants), each monoclonal antibody is directed against a single determinant on the antigen. In addition to their specificity, the benefit of monoclonal antibodies is that they are synthesized by hybridoma culture and are not contaminated by other immunoglobulins. The modifier "monoclonal" indicates the characteristics of an antibody, which is obtained from a substantially uniform antibody population, and it should not be interpreted as requiring any special method to produce antibodies.

In the present invention, the terms "antibody" and "immunoglobulin" are heterotetrameric glycoproteins of about 150,000 daltons with the same structural characteristics, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has a variable region (VH) at one end followed by a number of constant regions. Each light chain has a variable region (VL) at one end and a constant region at its other end; the constant region of the light chain is aligned with the first constant region of the heavy chain, and the light chain variable region is aligned with the variable region of the heavy chain.

In the present invention, the term "variable" refers to the fact that certain portions of the variable regions differ extensively in sequence among antibodies and are responsible for the binding specificity of each particular antibody for its particular antigen. However, the variability is not evenly distributed through the variable regions of antibodies. It is concentrated in three segments called complementarity determining regions (CDRs) or hypervariable regions both in the light chain and the heavy chain variable regions. The more conserved portions of the variable regions are called the framework regions (FR). The variable regions of native heavy and light chains each comprise four FR regions, largely adopting a p-fold configuration, connected by three CDRs, which form loops connecting, and in some cases forming part of the p-fold structure. The CDRs in each chain are held together in close proximity by the FR regions and, with the CDRs from the other chain, contribute to the formation of the antigen binding site of antibodies (see Kabat et al., NIH Publ. No. 91-3242, Volume I, Pages 647-669 (1991)). The constant regions are not involved directly in binding an antibody to an antigen, but they exhibit various effector functions, such as antibody-dependent cytotoxicity involved in the antibody.

In the present invention, the term "anti-human IL-5 antibody", "anti-human IL-5 mAb". "anti-human IL-5 monoclonal antibody" or "monoclonal antibody that binds to human IL-5" refer to monoclonal antibodies capable of binding to human IL-5 antigen. Preferably, the human IL-5 antigen has the amino acid sequence shown in SEQ ID NO: 1. Further, the anti-human IL-5 monoclonal antibody of the present invention can block the binding of IL-5 to IL-5RA.

In the present invention, the term "chimeric antibody" refers to an antibody that comprises heavy and light chain variable region sequences from one species and constant region sequences from another species, such as an antibody having mouse heavy and light chain variable regions linked to human constant region.

In the present invention, the term "humanized antibody" means that the CDRs are derived from a non-human (preferably, mouse) antibody, while the remaining parts (including framework regions and constant regions) are derived from human antibody. In addition, framework region residues may be altered to preserve binding affinity.

In the present invention, any suitable expression vector may be used, such as pTT5, pSECtag series, pCDNA series vectors, and other vectors used in mammalian expression systems. The expression vector comprises fusion DNA sequences linked to proper transcription and translation regulatory sequences.

In the present invention, the applicable host cell is a cell comprising the above expression vector, which may be a eukaryotic cell, for example, a mammalian or insect host cell culture system used for expressing the fusion protein of the present invention; CHO (Chinese Hamster Ovary), HEK293, COS, BHK, SP2/0, NIH3T3 and the like may be applied to the present invention. And it may also be a prokaryotic cell comprising the above expression vector, such as E. coli and so on.

The anti-human IL-5 monoclonal antibody in the present invention may be combined with pharmaceutically acceptable carriers to form pharmaceutical preparation compositions so as to exert a more stable therapeutic effect. These preparations can ensure the conformational integrity of the amino acid core sequences of the anti-human IL-5 monoclonal antibody disclosed in the present invention, and meanwhile protect the multifunctional groups of the protein from degradation (including but not limited to aggregation, deamination, or oxidation). Generally, for a liquid preparations, it can usually be kept stable for at least one year at 2° C.-8° C., and for a lyophilized preparation, it can be stable for at least six months at 30° C. The anti-human IL-5 monoclonal antibody preparation may be a preparation commonly used in the pharmaceutical field such as suspension, water needle, or a lyophilized preparation, and preferably water needle or lyophilized preparation. For the water-needle or lyophilized preparation of the anti-human IL-5 monoclonal antibody according to the present invention, pharmaceutically acceptable carriers include, but not limited to, surfactants, solution stabilizers, isotonicity adjusting agents, and buffers or a combination thereof. The surfactants preferably include but not limited to, nonionic surfactants such as polyoxyethylene sorbitan fatty acid ester (Tween 20 or 80); poloxamer (e.g. poloxamer 188); Triton; sodium dodecyl sulfate (SDS), sodium lauryl sulfate; tetradecyl, linoleyl or octadecyl sarcosine; Pluronics; MONAQUAT™, etc., which are added in an amount such that the granulation tendency of the anti-human IL-5 monoclonal antibody is minimized. The solution stabilizers preferably include but not limited to, one of the following: sugars, for example, reducing sugars and non-reducing sugars; amino acids, for example, monosodium glutamate or histidine; alcohols, for example, triols, higher sugar alcohols, propylene glycol, polyethylene glycol and the like, or a combination thereof. The solution stabilizer should be added in an amount such that the final formed preparation remains stable for a period of time that is considered stable by those skilled in the art. Isotonicity adjusting agents preferably include but not limited to, one of sodium chloride and mannitol, or a combination thereof. The buffers preferably include but not limited to, one of Tris, histidine buffer, and phosphate buffer, or a combination thereof.

The diseases mediated by eosinophil overexpression according to the present invention include but not limited to: asthma, granulomatosis with polyangiitis, chronic obstructive pulmonary disease (COPD), nasal polyps, allergic dermatitis, hypereosinophilia syndrome (HES) and so on.

The following examples and experimental examples further illustrate the present invention and should not be construed as limiting the present invention. The examples do not include a detailed description of traditional methods, such as those methods of constructing vectors and plasmids, methods of inserting genes encoding proteins into such vectors and plasmids and methods of introducing plasmids into host cells. Such methods are well known to those of ordinary skill in the art, and have been described in many publications, including Sambrook, J., Fritsch, E. F. and Maniais, T. (1989) Molecular Cloning: A Laboratory Manual, 2nd edition, Cold spring Harbor Laboratory Press.

Example 1 Preparation or IL-5 Antigen and Positive Control Antibody

The human IL-5 antigen sequence has the amino acid sequence as shown in SEQ ID NO: 1. The above amino acid sequence was codon optimized, and then a 6xHis tag was added to the end of the human IL-5 encoding genes. The genes were synthesized and then constructed into a pTT5 transient transfection vector (purchased from NRC biotechnology Research Institute). According to standard operating procedures, the above-described vector was transfected into HEK293 cells (purchased from NRC biotechnology Research Institute) and cultured in Freestyle 293 Expression Medium (purchased from Gibco). After 5 days, the expressed human IL-5-His-tag antigen was purified from the cell supernatant. The first step of purification was performed on a nickel affinity chromatography column, followed by refined purification by ion exchange chromatography. Finally the purity of the prepared human IL-5-His-tag was analyzed by SDS-PAGE, and the biological activity of the human IL-5-His-tag was determined by TF-1 cells. The purity of the final purified human IL-5-His-tag may reach more than 95%, and the biological activity was not significantly different from similar products on the market. The positive control antibody Nucala (Mepolizumab) was purchased from GSK/100 mg. Another positive control antibody hu39D10 was prepared according to the sequence disclosed in U.S. Pat. No. 9,505,82662, wherein the heavy chain was from SEQ ID NO: 2 in U.S. Pat. No. 9,505,82662, and the light chain was from SEQ ID NO: 8 in U.S. Pat. No. 9,505,82662. The heavy chain constant region was selected from human IgG4 (S228P). The antibody genes were synthesized and then constructed into the pTT5 vector, expressed using the HEK293E system (purchased from NRC biotechnology Research Institute), and then purified with Protein A affinity chromatography.

Wherein, the method of detecting the biological activity of human IL-5-His-tag using TF-1 cells is described as follows: TF1 cells (purchased from ATCC® CRL-2003™) in the logarithmic growth phase were washed twice with 37° C., pre-warmed RPMI1640 medium (purchased from Gibco), centrifuged at 300 g for 5 min each time; TF1 cells were counted, adjusted to a proper density with RPMI1640 medium containing 10% FBS, inoculated into a 96-well plate, $10^4$ cells/150 µl/well; human IL-5 was subjected to gradient dilution in RPMI1640 medium containing 10% FBS; then added into the above 96-well cell culture plate, 50 µl/well, with three replicate wells for each concentration. The remaining wells of the 96-well plate were filled with 200 µl/well of distilled water. The cells were incubated and cultured in a 37° C., 5% $CO_2$ incubator for 3 days. After 3 days, 20 µl CCK-8 solution (purchased from Dojindo) was added to each well of the 96-well cell culture plate, and the cells were cultured in a 37° C. incubator for another 8 hours. After well mixed, The OD450 values of the cultural fluid were read with a microplate reader, and GraphPad Prism6 was used to perform data analysis, prepare graphs, and calculate EC50.

Example 2 Immunization of Mice with IL-5 Antigen and Preparation and Screening of Hybridomas The human IL-5-His-tag antigen prepared in Example 1 was diluted with normal saline to an proper concentration, mixed with an equal volume of Freund's complete adjuvant, fully phaco-emulsified, and then administrated to 4-5 weeks old Balb/c mice (purchased from Shanghai Lingchang Biotechnology Co., Ltd., animal production license number: SCXK (Shanghai) 2013-0018) by multipoint subcutaneous injection, with 50 µg antigen/100 µl per mouse. Three weeks later, an equal amount of protein was mixed with an equal volume of Freund's incomplete adjuvant, fully phaco-emulsified, and then administrated to mice by multipoint subcutaneous immunization. Such immunization was repeated two weeks later. On the seventh day after the third immunization, one drop of blood was collected from each of the mice to separate serum, and the serum titer was determined by ELISA. For mice with serum antibody titers>100000, rush immunization was performed one week after the titer determination: injection of 10 µg antigen protein/100 µl normal saline/mouse by tail vein.

Wherein, the method of determining serum titer by ELISA is described as follows: IL-5-His-tag was diluted to 1000 ng/ml with sodium carbonate buffer (1.59 g $Na_2CO_3$ and 2.93 g $NaHCO_3$ dissolved in 1 L pure water), then added to the ELISA plate at 100 µl per well; incubated at room temperature for 4 hours. The plate was washed with phosphate buffer containing 0.05% Tween-20 (abbreviated as PBST: $KH_2PO_4$ 0.2 g, $Na_2HPO_4.12H_2O$ 2.9 g, NaCl 8.0 g, KCl 0.2 g, Tween-20 0.5 ml, pure water added to 1000 ml); and blocked by adding PBST containing 1% bovine serum albumin (BSA) to each well: the plate was washed with PBST, added with the gradiently diluted mouse serum, and incubated for a proper time; the plate was washed with PBST, added with a properly diluted HRP-labeled goat anti-mouse secondary antibody, and incubated for a proper time. After the plate was washed, the chromogenic solution (chromogenic substrate solution A: sodium acetate trihydrate 13.6 g, citric acid monohydrate 1.6 g, 30% hydrogen peroxide 0.3 ml, pure water 500 ml; chromogenic substrate solution B: ethylenediaminetetraacetic acid disodium 0.2 g, citric acid-monohydrate 0.95 g, glycerol 50 ml, TMB: 0.15 g dissolved in 3 ml DMSO, pure water 500 ml; solution A and solution B were mixed well in equal volumes before use) was used for color development, and a stop solution (2M sulfuric acid solution) was applied to stop the color reaction. The OD450 values were read with a microplate reader, and GraphPad Prism6 was used to perform data analysis, prepare graphs, and calculate serum titers.

The spleen cells of the mice were taken for fusion three days after the rush immunization. Hybridoma sp2/0 cells in good-growth condition (derived from the Cell Bank of the Typical Cell Culture Collection Committee of the Chinese Academy of Sciences) were cultured in a 37° C., 5% $CO_2$ incubator and the medium was renewed the day before fusion. The fusion and screening process was as follows: the spleens of the mice were taken, ground, washed and counted. The spleen cells and sp2/0 cells were mixed in a ratio of 2:1, centrifuged at 1500 rpm for 7 minutes. The supernatant was discarded. Under the condition of centrifugation at 1000 rpm for 5 min, 20 ml of cell fusion buffer (purchased from BTX) was added to wash the cells three times. The cell pellet was suspended in the cell fusion buffer at a density of $1\times10^7$ cells/ml. 2 ml of cell suspension was added to the fusion pool placed on the electrofusion machine ECM2001, and subjected to electrofusion according to certain conditions (AC60V, 30S; DC1700V, 40 μS, 3X; POST AC60V, 3S) within 30 seconds. After electrofusion, the fused cells were gently transferred to a 37° C., pre-warmed RPMI1640 medium containing 10% serum (purchased from Gibco), and standed at room temperature for another 60 minutes. 100 d/well, the cells were inoculated into a 96-well plate at $10^4$ cells/well. The next day, each well was supplemented with 100 μl of RPMI1640 medium containing 2×HAT (purchased from Gibco) and 10% serum. On the fourth day after the fusion, half of the medium was renewed once with RPM1640 medium containing 1×HAT and 10% serum. On the seventh day after the fusion, the medium was completely renewed once with RPM1640 medium containing 1×HAT and 10% serum. On the ninth day after the fusion, samples were taken for ELISA assay. Positive hybridoma clones were selected and expanded in a 24-well plate and subcloned by limiting dilution. Hybridoma strains that stably express the antibody of interest were obtained, and then preservation and library construction was performed. The obtained stable cell lines were cultured in serum-free medium HybriGRO SF (purchased from Corning) for 7 days. Then murine anti-human IL-5 monoclonal antibody was purified from the culture supernatant using Protein A/G affinity chromatography.

Example 3 Determination of Relative Affinity of Murine Anti-Human IL-5 Monoclonal Antibody Against IL-5 Antigen In this example, 40 purified murine anti-human IL-5 monoclonal antibodies obtained in Example 2 were analyzed by ELISA. For the experimental method, refer to the second paragraph of Example 2, except that the IL-5-His-tag was diluted to 100 ng/ml with sodium carbonate buffer.

The results are shown in FIG. 1. According to the EC50 data, the antibodies with higher relative affinity were selected (Lower EC50 indicates higher relative affinity), and totally 10 antibodies here (No. 4-6, 10, 13, 22, 26, 32, 41, 45, 46, 47) were advanced to next screening step.

Example 4 Determination of the Inhibitory Effect of Murine Anti-Human IL-5 Monoclonal Antibody on IL-5-Induced TF-1 Cells Proliferation In this example, the cell-level functional evaluation of the murine anti-human IL-5 monoclonal antibodies selected in Example 3 was performed by the following method: TF1 cells in the logarithmic growth phase were washed twice with 37° C., pre-warmed RPMI1640 medium, centrifuged at 1000 rpm for 5 min. The TF1 cells were counted, suspended with RPMI1640 medium containing 10% FBS to a proper density, and inoculated into a 96-well plate, $10^4$ cells/150 μl/well; human IL-5 protein (purchased from Beijing Yiqiao Shenzhou) was added to RPMI1640 medium containing 10% FBS to reach a concentration of 40 ng/ml; then the murine anti-human IL-5 monoclonal antibodies were diluted with the IL-5-containing medium to a proper concentration, and then serially diluted 9 times using proper echelon dilution. Meanwhile, Nucala (Mepolizumab) was used as a positive control, and human IgG1 isotype antibody that does not bind to IL-5 was used as a negative control. The diluted antibodies were added to the above 96-well cell culture plate containing TF1 cells, 50 μl/well. The remaining wells of the 96-well plate was filled with 200 μl/well of distilled water; the cultural solutions in the plate were incubated and cultured in a 37° C., 5% $CO_2$ incubator for 3 days. After 3 days, 20 μl CCK-8 solution was added to each well of the 96-well cell culture plate, and cultured in a 37° C. incubator for another 8 hours. After well mixed, the OD450 values of the cultural solutions were read with a microplate reader, and GraphPad Prism6 was used to perform data analysis, prepare graphs, and calculate EC50. Upon evaluation of the above preferred murine anti-human IL-5 monoclonal antibodies at cellular level, the antibodies with superior functional activity were selected for the next experiment.

Example 5 Determination of Nucleotide and Amino Acid Sequences of Murine Anti-Human IL-5 Monoclonal Antibody According to the above screening results of ELISA and functional experiment at cellular level, clones No. 4-6, 13, 22, 26, 32, 41, 45, 46, 47 were finally picked as lead antibodies. Total RNA was extracted from hybridoma monoclonal cell strains corresponding to the above monoclonal antibodies using Trizol (purchased from Life technologies). The mRNA was reverse transcribed into cDNA using a reverse transcription kit (purchased from Takara). By the primer combination reported in the literature (Antibody Engineering, Volume 1, Edited by Roland Kontermann and Stefan Dübel; the sequence of the combined primers from page 323), the genes of light chain variable region and heavy chain variable region of the murine anti-human IL-5 monoclonal antibody were amplified by PCR, then the PCR products were cloned into the pMD18-T vector and the variable region gene sequences were sequenced and analyzed. After comparative analysis of the variable region sequences of each clone, it was found that the sequences of antibody No. 4-6 were more suitable for humanization. So clone No. 4-6 was selected as the final candidate antibody. The sequence information is as follows: the heavy chain variable region gene sequence is 357 bp in length, encoding 119 amino acid residues; the nucleotide sequence is shown in SEQ ID NO: 2, and the amino acid sequence is shown in SEQ ID NO: 3. The light chain variable region gene sequence is 321 bp in length, encoding 107 amino acid residues; the nucleotide sequence is shown in SEQ ID NO: 4, and the amino acid sequence is shown in SEQ ID NO: 5. The amino acid sequences were aligned in GenBank, both of which are consistent with the characteristics of the mouse IgG variable region gene.

Example 6 Humanization of Murine Anti-Human IL-5 Monoclonal Antibody

The heavy chain variable region and light chain variable region of the murine antibody No. 4-6 were spliced to the light and heavy chain constant region of human IgG1 by overlapping PCR to construct the chimeric antibody No. 4-6 (4-6-Chimeric).

The amino acid sequences of the heavy chain variable region and the light chain variable region were analyzed, and three complementarity-determining regions (CDRs) and four frame regions (FRs) of the antibody No. 4-6 were identified according to the Kabat rule. Wherein, the amino acid sequences of the heavy chain complementarity determining regions are: H-CDR1: NHHIN (SEQ ID NO: 6), H-CDR2: YINPYNDYSRYNQKFKG (SEQ ID NO: 7) and H-CDR3: DYGNFWYFDV (SEQ ID NO: 8), and the amino acid sequences of the light chain complementarity determining regions are: L-CDR1: KASQDINSYLS (SEQ ID NO: 9), L-CDR2: RADRLID (SEQ ID NO: 10) and L-CDR3: LQYDDFPYT (SEQ ID NO: 11).

By homology comparison with human IgG germline sequence (Germline) at NCBI IgBLAST, IGHV1-46*01 was selected as the heavy chain CDR graft template. The heavy chain CDRs of murine antibody No. 4-6 were transplanted into the IGHV1-46*01 framework regions to construct a heavy chain CDR-grafted antibody. Similarly, by homology comparison with human IgG germline sequence, IGKV1-39*01 was selected as the light chain CDR graft template, and the light chain CDRs of the murine antibody No. 4-6 were transplanted into the IGKV1-39*01 framework regions to construct a light chain CDR-grafted antibody. The obtained antibody was defined as 4-6-Grafted. Meanwhile, on this basis, some amino acid sites in the framework region were subjected to back mutation. Back mutation refers to mutation of certain amino acid in the human framework region to an amino acid at the same position in the murine framework region. When back mutation was performed, the amino acid sequence was encoded by Kabat numbering system and the positions were indicated by Kabat numbering. Preferably, for the heavy chain variable region sequence, M at position 48 according to Kabat numbering was back mutated to murine 1, V at position 67 was back mutated to A. M at position 69 was back mutated to L, R at position 71 was back mutated to V, and V at position 78 was back mutated to A. For the light chain variable region sequence, Y at position 36 according to Kabat numbering was back mutated to I, L at position 46 was back mutated to T, Y at position 49 was back mutated to H, and T at position 69 was back mutated to Q. The above variable region gene sequences were codon-optimized and synthesized according to the codon usage preference of *Cricetulus griseus* by Suzhou Jinweizhi Company. The synthesized humanized variable region sequence was connected to the human IgG1 constant region, and the obtained antibody was defined as humanized antibody No. 4-6 (4-6-Humanized).

The genes of the above light and heavy chain of the humanized antibody No. 4-6 were constructed into the pTT5 expression vector, and the above light and heavy chain expression vectors were combined and subjected to transient transfection and antibody expression using the HEK293 system. The HEK293 cells were cultured in Free Style 293 Expression Medium. The plasmid was transferred into the cells by PEI transfection. 5 days later, the cell supernatant was collected and subjected to Protein A affinity chromatography to obtain purified antibodies.

Finally, the heavy chain variable region gene sequence of 4-6-Humanized is 357 bp in length, encoding 119 amino acid residues, the nucleotide sequence thereof is shown in SEQ ID NO: 12, and the amino acid sequence is shown in SEQ ID NO: 13; the light chain variable region gene sequence of 4-6-Humanized is 321 bp in length, encoding 107 amino acid residues, the nucleotide sequence thereof is shown in SEQ ID NO: 14, and the amino acid sequence is shown in SEQ ID NO: 15. After being connected to the human IgG1 constant region, a heavy chain of 4-6-Humanized of 449 amino acids (the sequence is shown in SEQ ID NO: 16) and a light chain of 4-6-Humanized of 214 amino acids (the sequence is shown in SEQ ID NO: 17) were finally obtained.

Figure 3:
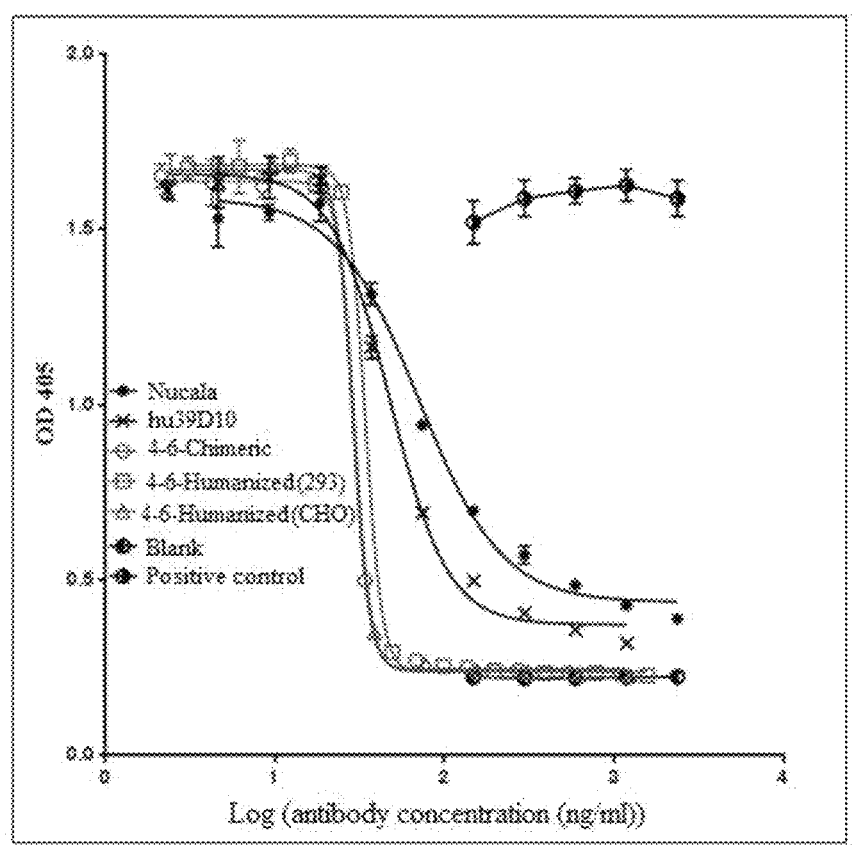
FIG. 3 is a graph showing the results of inhibiting IL-5-induced TF-1 cell proliferation by 4-6-Humanized and 4-6-Chimeric, where in the blank control, IL-5 was absent but an irrelevant isotype control antibody was added to determine the lower limit of the cell proliferation; in the positive control, both IL-5 and an irrelevant isotype control antibody were added to determine the upper limit of the cell proliferation; the irrelevant isotype control antibody means that the control antibody does not recognize IL-5, but it has the same constant region as the antibody to be tested.

Example 7 Determination of Inhibitory Effects of Anti-Human IL-5 Monoclonal Antibodies of the Present Invention on IL-5-Induced TF-1 Cell Proliferation In this example, the functions of the humanized antibody No. 4-6 (4-6-Humanized) and the chimeric antibody No. 4-6 (4-6-Chimeric) were compared in detail by the inhibition experiment on TF-1 cell proliferation. The procedures were carried out according to Example 4. The experiment results are shown in FIG. 3 that the IC50 of Nucala, hu39D10, 4-6-Chimeric, 4-6-Humanized (293) and 4-6-Humanized (CHO) (prepared using ExpiCHO Expression System, purchased from Thermo Scientific, following the operation instructions provided by the supplier) for inhibiting IL-5-induced TF-1 cell proliferation were 70.85 ng/ml, 47.62 ng/ml, 28.93 ng/ml, 34.12 ng/ml and 29.37 ng/ml, respectively. The above results show that the humanized antibody No. 4-6 (4-6-Humanized) and the chimeric antibody No. 4-6 (4-6-Chimeric) have almost identical ability to inhibit the IL-5-induced TF-1 cell proliferation, indicating that the humanization is successful. And 4-6-Humanized and 4-6-Chimeric of the present invention have significantly stronger functional activities than those of the positive control antibodies Nucala and hu39D10.

Example 8 Determination of Abilities of Anti-Human IL-5 Monoclonal Antibodies of the Present Invention to Block Interaction Between IL-5 and IL-5RA In this embodiment, the abilities of the humanized antibody No. 4-6 (4-6-Humanized) and the chimeric antibody No. 4-6 (4-6-Chimeric) to block the interaction between IL-5 and IL-5RA was evaluated by ELISA. First, at the gene level, the genes of L-5 and the extracellular domain (ECD) of IL-5RA (IL-5RA, Interleukin-5 receptor subunit alpha, source of amino acid sequence: Suzhou Jinweizhi Company to carry out gene synthesis work) were fused with the Fc segment of human IgG1 by recombinant PCR, respectively, then constructed into expression vectors of IL-5-hFc and IL-5RA-ECD-hFc using pTT5, which are subjected to transient expression in HEK293E cells and purified by Protein A affinity chromatography. Then the enzyme-labeled plate was coated with human IL-5-hFc prepared in-house, added with a mixture of biotinylated IL-5RA-ECD-hFc and gradiently diluted antibodies to be tested after blocking. After incubation for a period of time, the plate was washed and Streptavidin-HRP was added finally for color development detection. Wherein, the amino acid sequence of the heavy chain variable region sequence of the control antibody 4-4-Humanized is shown in SEQ ID NO: 18; the amino acid sequence of the light chain variable region sequence is shown in SEQ ID NO: 19; the constant region sequence is identical to that of 4-6-Humanized of the present invention.

Figure 4:
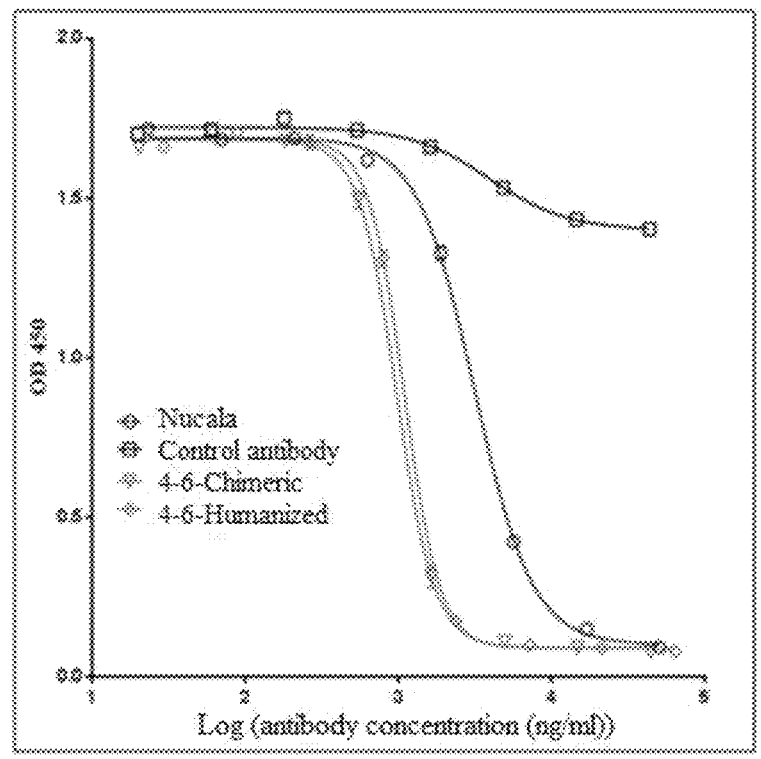
FIG. 4 is a graph showing the results of blocking the interaction between IL-5 and its receptor by 4-6-Humanized and 4-6-Chimeric, where the control antibody 4-4-Humanized is an antibody that can bind to IL-5 but not block the interaction between IL-5 and its receptor.

The experiment results are shown in FIG. 4. The IC50 of Nucala, 4-6-Chimeric and 4-6-Humanized for blocking the interaction between IL-5 and its receptor were 3172 ng/ml, 979.9 ng/ml and 1097 ng/ml, respectively, indicating that 4-6-Chimeric and 4-6-Humanized of the present invention have significantly stronger abilities to block the interaction between IL-5 and its receptor than that of the positive control antibody Nucala.

Example 9 Determination of Affinities of Anti-Human IL-5 Monoclonal Antibodies of the Present Invention Against Antigen The affinities of the humanized antibody No. 4-6 (4-6-Humanized) and the chimeric antibody No. 4-6 (4-6-Chimeric) for IL-5 were determined by Biacore T200 (GE healthcare), respectively. The specific experimental method was as follows: A CM5 sensor chip (GE healthcare) was activated with a Amine Coupling Kit (GE healthcare) and the Protein A/G fusion protein (Thermo Pierce) was immobilized on the chip with an lable amount of 2000 RU. FC3 (Flow cell 3) was a reference channel, and FC4 (Flow cell 4) was a sample channel. The humanized antibody No. 4-6 (4-6-Humanized), the chimeric antibody No. 4-6 (4-6-Chimeric) or control antibodies (Nucala and hu39D10) were captured separately on the FC4 channel, followed by injection of various concentrations of human IL-5 protein (purchased from Beijing Yiqiao Shenzhou). The cycling conditions were as follows: the analyte was injected at 50 µl/min for 4 min in all channels of the FC; the dissociation time was 20 min; 6 M guanidine hydrochloride (Sinopharm Group Chemical Reagent Co., Ltd.) was injected at a rate of 10 µl/min for 30 s for surface regeneration, and then the difference between the signals of the captured antibodies and the antibody-free signals as well as the interaction affinity were calculated using Biacore T200 Evaluation Software Ver 1.0.

The experimental results are shown in Table 1. The results indicate that the affinities of the humanized antibody No. 4-6 (4-6-Humanized) and the chimeric antibody No. 4-6 (4-6-Chimeric) of the present invention for IL-5 are higher than that of the positive antibody Nucala (Mepolizumab), which currently dominates the market. This is mainly because 4-6-Humanized and 4-6-Chimeric of the present invention can bind to IL-5 more rapidly than the positive control antibody. Besides, both of them have high affinities of 10 pM which are comparable to another positive control antibody hu39D10.

TABLE 1

Determination of affinities of anti-human IL-5 monoclonal antibodies of the present invention against human IL-5

| | Kon (1/Ms) | Koff (1/s) | KD (M) |
| --- | --- | --- | --- |
| Nucala (Mepolizumab) | 7.34E+05 | 1.47E−04 | 2.01E−10 |
| hu39D10 | 1.15E+07 | 1.56E−04 | 1.36E−11 |
| 4-6-Chimeric | 1.51E+07 | 1.96E−04 | 1.30E−11 |
| 4-6-Humanized | 1.45E+07 | 1.91E−04 | 1.32E−11 |

Example 10 Epitope Analysis of Anti-Human IL-5 Monoclonal Antibody of the Present Invention The amino acid code of IL-5 is as follows:

```
                                            (SEQ ID NO: 1)
IPTEIPTSALVKETLALLSTHRTLLIANETLRIPVPVHKNHQLCTEEIFQ
GIGTLESQTVQGGTVERLFKNLSLIKKYIDGQKKKCGEERRRVNQFLDYL
QEFLGVMNTEWIIES.
```

Figures 5, 6:
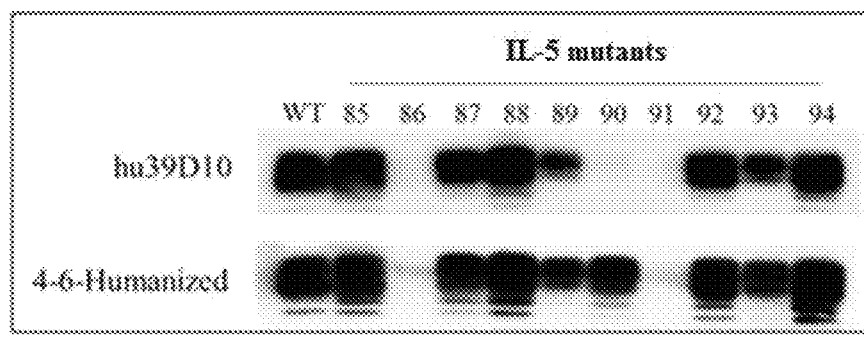
FIG. 5 is a graph showing the ELISA results of 4-6-Humanized antigen epitope analysis, where an OD450 below 0.5 was defined to indicate a significant weakening of the binding between the antibody and the antigen, and each value represented an average of four replicate wells.
FIG. 6 is a graph showing the results of western blot analysis of epitope of 4-6-Humanized.

According to reports in the literature, the underlined amino acids are critical for the interaction between IL-5 and its receptor. We conducted site-directed mutagenesis of these sites to mutate them into Alanine, respectively, then performed transiently expression of the 23 IL-5 mutants having his-Tag in HEK293E cells, and captured the IL-5 mutants (all the IL-5 mutants had a His-tag) in the expressed supernatant using a murine anti-His antibody. Then, the antibodies to be tested (Nucala, hu39D10 and 4-6-Humanized) were binded to the captured IL-5 mutants, which was then detected by Goat-anti-Human-Fc-Specific-HRP. If the antibody to be tested did not bind to a certain mutant, the mutation site was considered to be very important for the binding function of the antibody. The results are shown in FIG. 5. It was finally found that among all 23 mutants, only the mutations of 86C, 90R, 91R, 96F, 104L have significant effects on the binding of the tested antibodies, and these five mutations have different effects on each antibody. The results are summarized in Table 2. We can find that the epitopes of the humanized antibody No. 4-6 (4-6-Humanized) of the present invention are different from those of Nucala and hu39D10.

TABLE 2

Binding effects of anti-human IL-5 monoclonal antibody of the present invention on IL-5 mutants

| | Nucala (Mepolizumab) | hu39D10 | 4-6-Humanized |
| --- | --- | --- | --- |
| 86C | − | − | − |
| 90R | + | − | + |
| 91R | + | − | − |
| 96F | − | − | − |
| 104L | − | − | − |

Note:
"+" indicates that the site mutation has no obvious effect on the binding of the antibody,
"−" indicates that the site mutation can significantly weaken or completely eliminate the binding of the antibody to the mutant.

Westernblot was applied to further confirm the above ELISA epitope analysis results. The operation method of Westernblot was implemented according to the scheme provided by Cell Signalling Technologies. Gel electrophoresis and transfer system as well as chemiluminescence imaging system were purchased from Bio-Rad. Western blot analysis was performed on the 10 mutants at positions 85 to 94, using Hu39D10 and 4-6-Humanized antibody as primary antibody, respectively, and HRP-conjugated goat anti-human Fc-Specific enzyme-labeled antibody as secondary antibody. Finally, the development step was carried out by chemiluminescence method and the chemiluminescence imaging system was used to take photos. The results of the experiment are shown in FIG. 6. Mutation of any amino acid of 86C, 90R and 91R can lead to failure of hu39D10 to bind IL-5, and mutation of any amino acid of 86C and 91R can cause 4-6-Humanized to fail to bind IL-5.

Example 11 Verification of Species Cross-Reactivity of Anti-Human IL-5 Monoclonal Antibody of the Present Invention In order to provide information for subsequent pharmacological and toxicological studies, this example validated the species cross-reactivity of 4-6-Humanized antibody. IL-5 genes of rat, mouse, guinea pig and rabbit were synthesized and constructed into the pTT5 transient vector, respectively ( the mouse number is P04401, the rat number is Q08125, the guinea pig number is O08987, and the rabbit number is G1SL79), and then transiently expressed in HEK293E. A murine anti-His antibody was used to capture and express IL-5 of different species in the supernatant (all IL-5 of different species have a His-tag), and the antibodies to be tested (Nucala, hu39D10 and 4-6-Humanized) were used to bind the captured IL-5, and then Goat-anti-Human-Fc-Specific-HRP was used to detect the binding of the antibody to be tested to IL-5. The experimental results are shown in Table 3. Both 4-6-Humanized of the present invention and hu30D10 can effectively recognize the IL -5 in guinea pigs and mice, but have relatively weak binding abilities to IL-5 in rats. In addition, neither of them recognizes rabbit IL-5. Nucala does not recognize IL-5 in rats, mice, guinea pigs and rabbits, so the results are not shown here.

TABLE 3

Species cross-reactivity of anti-human IL-5 monoclonal antibody of the present invention

| | hu39D10 | | | | 4-6-Humanized | | | |
|---|---|---|---|---|---|---|---|---|
| Species | Human | Guinea pig | Mouse | Rat | Human | Guinea pig | Mouse | Rat |
| EC50 (ng/ml) | 78.03 | 53.14 | 61.84 | 132.1 | 83.89 | 55.76 | 52.13 | 2131 |

Example 12 Pharmacokinetic Study of Anti-Human IL-5 Monoclonal Antibody of the Present Invention The pharmacokinetics of 4-6-Humanized was evaluated by intravenous injection (I.V.) of rats in this example.

Rats weighing about 200 g were divided into groups of four. Each rat was intravenously injected with anti-human IL-5 monoclonal antibody or human IgG1 isotype control antibody at a dose of 1 mg. Blood was taken from the orbit at specific time after administration. The blood was naturally coagulated and centrifuged to separate serum. The antibody concentration in the serum was determined as follows: ELISA plate was coated with goat anti-human Fc segment antibody (purchased from Sigma; the antibody was subjected to species cross-adsorption treatment and did not bind rat endogenous antibody) at a concentration of 1000 ng/ml, 100 µl/well; blocked with PBST+1% BSA after coating and then added with a properly diluted rat serum. After a period of incubation, the plate was washed and finally HRP-labeled goat anti-human antibody (purchased from Sigma; the antibody was subjected to species cross-adsorption treatment and did not recognize rat endogenous antibody) was added. After another period of incubation, the plate was washed and added with a chromogenic solution for color development. The coloring reaction was stopped by a stop solution, and then OD450 was determined. The OD450 value was converted to antibody concentration according to a standard curve. GraphPad Prism6 was used to perform data collation and analysis and prepare graphs, and Phoenix software was used to calculate the half-life of antibody drugs in rats.

Figure 7:
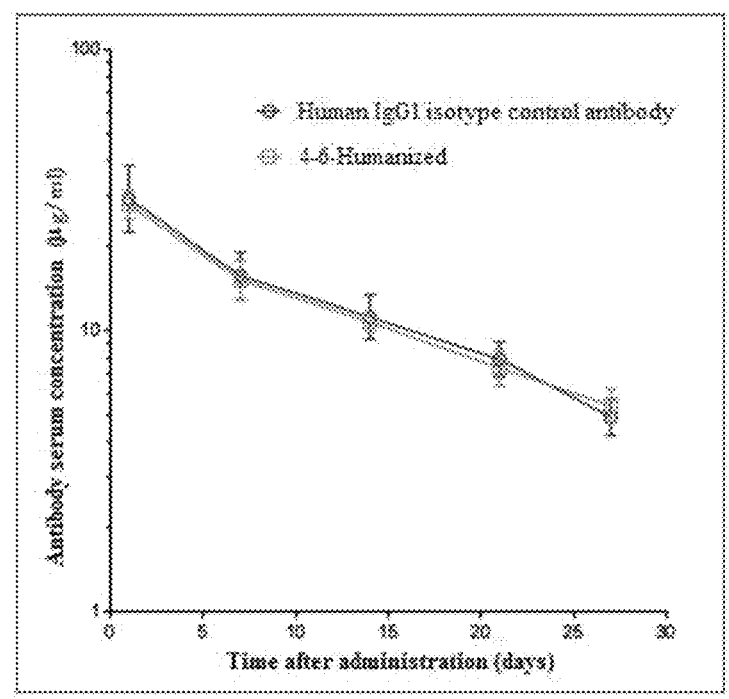
FIG. 7 is a graph showing the results of pharmacokinetic study of 4-6-Humanized.

As shown in FIG. 7, the pharmacokinetic results of intravenous injection in rats indicate that the half-life of 4-6-Humanized antibody in rats is basically equivalent to that of the human IgG1 isotype control antibody, which are 13.90 days and 12.65 days, respectively.

Example 13 In Vivo Pharmacodynamic Study of Anti-Human IL-5 Monoclonal Antibody of the Present Invention In this example, an ovalbumin-induced mouse asthma model was used to perform the in vivo pharmacodynamic study.

The experimental process was as follows: Balb/c mice were randomly divided into 6 groups, with 10 mice in each group. The groups were as follows: non-model control group, model control group. 4-6-Humanized antibody group (divided into a low-dose group and a high-dose group) and positive control antibody group. Then, Ovalbumin (purchased from Sigma) and Inject Alum (an immunoadjuvant, purchased from Termo Fisher) were mixed to prepare a suspension, which was intraperitoneally injected into mice on day 1 and day 14 (the negative control group was intraperitoneally injected with PBS) to sensitize the mice; on days 28, 29, and 30, the animals in the experimental groups were stimulated with aerosolized PBS solution containing 1% Ovalbumin to induce asthma in mice (in control groups, the mice were stimulated with aerosolized PBS). On day 20 and day 28 (2 h before the stimulation of mice by aerosolized Ovalbumin solution), the mice were administrated by subcutaneous injection. The dosage regimens were as follows: the non-model control group was injected with an antibody-free auxiliary solution, the model control group was injected with an antibody-free auxiliary solution, and the low-dose group and high-dose group of 4-6-Humanized antibody were injected with the anti-human IL-5 monoclonal antibody of the present invention at 0.4 and 2 mg/kg, respectively. And the positive control antibody group was injected with Reslizumab (trade name Cinqair, purchased from Teva Pharmaceutical Industries) at 2 mg/kg. On day 32, the animals were bled, and the content of eosinophils in the blood samples was measured by flow cytometry (the blood cells were stained with fluorophore APC-eFluor780-labeled anti-Ly-6G antibody, PE-labeled anti-CD193 antibody, and eFluor 506-labeled CD45 antibody. The cells that were positive for staining with all three antibodies were considered to be eosinophils. The above fluorescently labeled anti-Ly-6G antibody and anti-CD193 antibody were purchased from eBioscience, and the anti-CD45 antibody was purchased from BioLegend).

The data collection and statistical analysis methods were as follows: The number of eosinophils in animals of each group was analyzed by GraphPad Prism 6 software. The difference between groups was compared by T-test, and $p<0.05$ was considered to be a significant difference, $p<0.01$ was considered to be a very significant difference.

Figure 8:
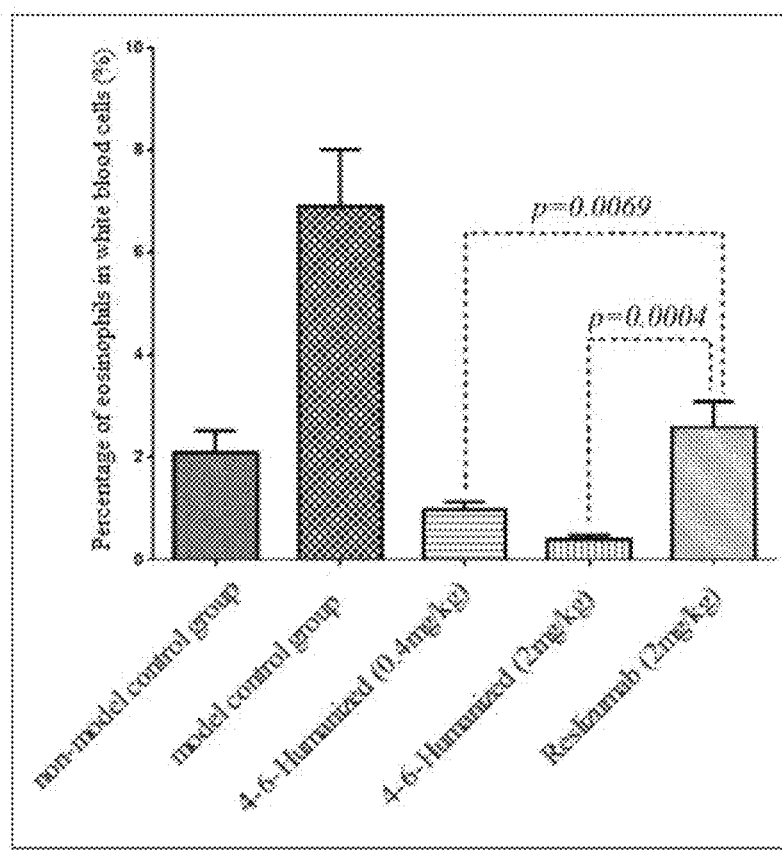
FIG. 8 is a graph showing the results of in vivo pharmacodynamic study of 4-6-Humanized.

The experimental results are shown in FIG. 8. Compared with the non-model group, the content of eosinophils in the blood samples was significantly increased after modeling, indicating that the modeling was successful. Compared with the model control group, the proportions of eosinophils in the low-dose group and high-dose group of 4-6-Humanized antibody as well as the positive control antibody group were significantly reduced, and compared with the positive control antibody group, p-values of the 4-6-Humanized antibody low-dose group and high-dose group were 0.0069 and 0.0004, respectively, having a very significant difference, indicating that the efficacy of 4-6-Humanized antibody in vivo is superior to that of the positive control antibody Reslizumab.

What is claimed is:

1. A monoclonal antibody that specifically binds to human IL-5, wherein said monoclonal antibody comprises:
   (a) a heavy chain, the heavy chain comprising heavy chain complementarity determining regions H-CDR1, H-CDR2, H-CDR3, the H-CDR1 having the amino acid sequence as shown in SEQ ID NO: 6, the H-CDR2 having the amino acid sequence as shown in SEQ ID NO: 7, the H-CDR3 having the amino acid sequence as shown in SEQ ID NO: 8, and
   (b) a light chain, the light chain comprising light chain complementarity determining regions L-CDR1, L-CDR2, L-CDR3, the L-CDR1 having the amino acid sequence as shown in SEQ ID NO: 9, the L-CDR2 having the amino acid sequence as shown in SEQ ID NO: 10, and the L-CDR3 having the amino acid sequence as shown in SEQ ID NO: 11.

2. The monoclonal antibody of claim 1, wherein said monoclonal antibody is a murine antibody, a chimeric antibody, or a humanized antibody.

3. The monoclonal antibody that binds to human of claim 1, wherein the heavy chain of the monoclonal antibody comprises a heavy chain variable region having the amino acid sequence as shown in SEQ ID NO: 3, and the light chain of the monoclonal antibody comprises a light chain variable region having the amino acid sequence as shown in SEQ ID NO: 5; or the heavy chain of the monoclonal antibody comprises a heavy chain variable region having the amino acid sequence as shown in SEQ ID NO: 13, and the light chain of the monoclonal antibody comprises a light chain variable region having the amino acid sequence as shown in SEQ ID NO: 15.

4. The monoclonal antibody of claim 3, wherein the heavy chain of the monoclonal antibody has the amino acid sequence as shown in SEQ ID NO: 16, and the light chain has the amino acid sequence as shown in SEQ ID NO: 17.

5. An isolated nucleotide molecule, wherein the nucleotide molecule encodes the monoclonal antibody of claim 1.

6. The nucleotide molecule of claim 5, wherein the nucleotide molecule comprises:
   a nucleotide sequence that encodes a heavy chain variable region, wherein the nucleotide comprises the nucleotide sequence of SEQ ID NO: 2,
   a nucleotide sequence that encodes a light chain variable region, wherein the nucleotide comprises the nucleotide sequence of SEQ ID NO: 4;
   a nucleotide sequence that encodes a the heavy chain variable region, wherein the nucleotide comprises the nucleotide sequence of SEQ ID NO: 12, or
   a nucleotide sequence that encodes light chain variable region wherein the nucleotide comprises the nucleotide sequence of in SEQ ID NO: 14.

7. An expression vector, that comprises the nucleotide molecule of claim 5.

8. A host cell that comprises the expression vector of claim 7.

9. A method for preparing a monoclonal antibody that binds to human IL-5, the method comprising the following steps:
   (a) under expression conditions, cultivating the host cell of claim 8, thereby expressing the monoclonal antibody that binds to human IL-5;
   (b) isolating the monoclonal antibody that binds to human IL-5 of the step (a).

10. The method of claim 9, further comprising purifying the monoclonal antibody that binds to the human IL-5.

11. A pharmaceutical composition that comprises the monoclonal antibody that binds to human IL-5 of claim 1 and a pharmaceutically acceptable carrier.

12. A method for treating a disease mediated by eosinophil overexpression comprising administering to an individual in need thereof a monoclonal antibody of claim 1.

13. The method of claim 12, wherein the disease mediated by eosinophil overexpression comprises asthma, granulomatosis with polyangiitis, chronic obstructive pulmonary disease, nasal polyps, allergic dermatitis, or hypereosinophilia syndrome.

14. The method of claim 13, wherein the disease mediated by eosinophil overexpression is asthma.

15. The method of claim 13, wherein the disease mediated by eosinophil overexpression is granulomatosis with polyangiitis.

16. The method of claim 13, wherein the disease mediated by eosinophil overexpression is chronic obstructive pulmonary disease.

17. The method of claim 13, wherein the disease mediated by eosinophil overexpression is allergic dermatitis.

18. The method of claim 13, wherein the disease mediated by eosinophil overexpression is nasal polyps.

19. The method of claim 13, wherein the disease mediated by eosinophil overexpression is hypereosinophilia syndrome.

* * * * *

```
                           SEQUENCE LISTING

<160> NUMBER OF SEQ ID NOS: 19

<210> SEQ ID NO 1
<211> LENGTH: 115
<212> TYPE: PRT
<213> ORGANISM: Homo

<400> SEQUENCE: 1

Ile Pro Thr Glu Ile Pro Thr Ser Ala Leu Val Lys Glu Thr Leu Ala
1               5                   10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60

Val Glu Arg Leu Phe Lys Asn Leu Ser Leu Ile Lys Lys Tyr Ile Asp
65                  70                  75                  80

Gly Gln Lys Lys Lys Cys Gly Glu Glu Arg Arg Val Asn Gln Phe
                85                  90                  95

Leu Asp Tyr Leu Gln Glu Phe Leu Gly Val Met Asn Thr Glu Trp Ile
            100                 105                 110

Ile Glu Ser
        115

<210> SEQ ID NO 2
<211> LENGTH: 357
<212> TYPE: DNA
<213> ORGANISM: Mus musculus

<400> SEQUENCE: 2
caggtccagc tgcagcagtc tggggccgag ctggtgaggc ctggggcctc agtgaagatt      60
tcctgcaagg cttttggcta caccttcaca aaccatcata taaactgggt gcagcagagg     120
cctggacagg gcctggactg gattggatat attaatcctt ataatgatta tagtaggtac     180
aaccagaagt tcaagggcaa ggccacattg actgtagaca atcctccag cacagcctat      240 atggagctta gcggcctgac atctgaagac tctgcagtct attactgtgc aagagactat     300
ggtaacttct ggtacttcga tgtctggggc gcaggacca cggtcaccgt ctcctca        357

<210> SEQ ID NO 3
<211> LENGTH: 119
<212> TYPE: PRT
<213> ORGANISM: Mus musculus

<400> SEQUENCE: 3

Gln Val Gln Leu Gln Gln Ser Gly Ala Glu Leu Val Arg Pro Gly Ala
1               5                   10                  15

Ser Val Lys Ile Ser Cys Lys Ala Phe Gly Tyr Thr Phe Thr Asn His
            20                  25                  30

His Ile Asn Trp Val Gln Gln Arg Pro Gly Gln Gly Leu Asp Trp Ile
        35                  40                  45

Gly Tyr Ile Asn Pro Tyr Asn Asp Tyr Ser Arg Tyr Asn Gln Lys Phe
    50                  55                  60
```

```
Lys Gly Lys Ala Thr Leu Thr Val Asp Lys Ser Ser Ser Thr Ala Tyr
 65                  70                  75                  80

Met Glu Leu Ser Gly Leu Thr Ser Glu Asp Ser Ala Val Tyr Tyr Cys
                 85                  90                  95

Ala Arg Asp Tyr Gly Asn Phe Trp Tyr Phe Asp Val Trp Gly Ala Gly
            100                 105                 110

Thr Thr Val Thr Val Ser Ser
            115
```

<210> SEQ ID NO 4
<211> LENGTH: 321
<212> TYPE: DNA
<213> ORGANISM: Mus musculus

<400> SEQUENCE: 4

```
gacatcaaga tgacccagtc tccatcttcc atgtatgcat ctctaggaga gagagtcact    60
atcacttgca aggcgagtca ggacattaat agctatttaa gctggatcca gcagaaacca   120
gggaaatctc ctaagaccct gatccatcgt gcagacagat tgatagatgg ggtcccatca   180
aggttcagtg gcagtggatc tgggcaagat tttctctctc ccatcagcag cctggagtat   240
gaagatatgg gaatttatta ttgtctacag tatgatgact tccgtacac gttcggaggg   300
gggaccaagc tggaaataaa a                                             321
```

<210> SEQ ID NO 5
<211> LENGTH: 107
<212> TYPE: PRT
<213> ORGANISM: Mus musculus

<400> SEQUENCE: 5

```
Asp Ile Lys Met Thr Gln Ser Pro Ser Ser Met Tyr Ala Ser Leu Gly
 1               5                  10                  15

Glu Arg Val Thr Ile Thr Cys Lys Ala Ser Gln Asp Ile Asn Ser Tyr
                 20                  25                  30

Leu Ser Trp Ile Gln Gln Lys Pro Gly Lys Ser Pro Lys Thr Leu Ile
             35                  40                  45

His Arg Ala Asp Arg Leu Ile Asp Gly Val Pro Ser Arg Phe Ser Gly
     50                  55                  60

Ser Gly Ser Gly Gln Asp Phe Ser Leu Thr Ile Ser Ser Leu Glu Tyr
 65                  70                  75                  80

Glu Asp Met Gly Ile Tyr Tyr Cys Leu Gln Tyr Asp Asp Phe Pro Tyr
                 85                  90                  95

Thr Phe Gly Gly Gly Thr Lys Leu Glu Ile Lys
            100                 105
```

<210> SEQ ID NO 6
<211> LENGTH: 5
<212> TYPE: PRT
<213> ORGANISM: Mus musculus

<400> SEQUENCE: 6

```
Asn His His Ile Asn
 1               5
```

<210> SEQ ID NO 7
<211> LENGTH: 17
<212> TYPE: PRT
<213> ORGANISM: Mus musculus

<400> SEQUENCE: 7

Tyr Ile Asn Pro Tyr Asn Asp Tyr Ser Arg Tyr Asn Gln Lys Phe Lys
1               5                   10                  15

Gly

<210> SEQ ID NO 8
<211> LENGTH: 10
<212> TYPE: PRT
<213> ORGANISM: Mus musculus

<400> SEQUENCE: 8

Asp Tyr Gly Asn Phe Trp Tyr Phe Asp Val
1               5                   10

<210> SEQ ID NO 9
<211> LENGTH: 11
<212> TYPE: PRT
<213> ORGANISM: Mus musculus

<400> SEQUENCE: 9

Lys Ala Ser Gln Asp Ile Asn Ser Tyr Leu Ser
1               5                   10

<210> SEQ ID NO 10
<211> LENGTH: 7
<212> TYPE: PRT
<213> ORGANISM: Mus musculus

<400> SEQUENCE: 10

Arg Ala Asp Arg Leu Ile Asp
1               5

<210> SEQ ID NO 11
<211> LENGTH: 9
<212> TYPE: PRT
<213> ORGANISM: Mus musculus

<400> SEQUENCE: 11

Leu Gln Tyr Asp Asp Phe Pro Tyr Thr
1               5

<210> SEQ ID NO 12
<211> LENGTH: 357
<212> TYPE: DNA
<213> ORGANISM: Artificial Sequence
<220> FEATURE:
<223> OTHER INFORMATION: heavy chain variable region

<400> SEQUENCE: 12
caggtgcagc tggtgcagtc cggcgctgag gtgaaaaagc ccggcgcctc cgtgaaggtg      60
tcctgcaaag cctccggcta caccttcacc aaccaccaca tcaactgggt gaggcaggct     120
cctggccagg gactggagtg gatcggctac atcaacccct acaacgacta ctccggtac     180 aaccagaagt tcaagggcag ggccaccctg accgtggaca gtccactcc caccgcctac     240 atggagctgt cctccctgag gtccgaggac accgccgtgt actactgcgc caggactac     300 ggcaacttct ggtacttcga cgtgtggggc cagggcaccc tggtgacagt gtcctcc       357

<210> SEQ ID NO 13
<211> LENGTH: 119
<212> TYPE: PRT
<213> ORGANISM: Artificial Sequence
<220> FEATURE:
<223> OTHER INFORMATION: heavy chain variable region

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

His Ile Asn Trp Val Arg Gln Ala Pro Gly Gln Gly Leu Glu Trp Ile
        35                  40                  45

Gly Tyr Ile Asn Pro Tyr Asn Asp Tyr Ser Arg Tyr Asn Gln Lys Phe
50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Gly Asn Phe Trp Tyr Phe Asp Val Trp Gly Gln Gly
                100                 105                 110

Thr Leu Val Thr Val Ser Ser
            115

<210> SEQ ID NO 14
<211> LENGTH: 321
<212> TYPE: DNA
<213> ORGANISM: Artificial Sequence
<220> FEATURE:
<223> OTHER INFORMATION: light chain variable region

<400> SEQUENCE: 14
gacatccaga tgacccagtc cccttccagc ctgtccgcta gcgtgggcga cagggtgacc      60
atcacctgca aggcctccca ggacatcaac tcctacctgt cctggatcca gcagaagccc     120
ggcaaggccc ccaagaccct gatccacagg gccgataggc tgatcgacgg cgtgccctcc     180
aggttttccg gctccggatc cggccaggac ttcaccctga ccatctcctc cctgcagccc     240
gaggacttcg ccacctacta ctgcctgcag tacgacgact cccctacac cttcggccag      300 ggcaccaagg tggagatcaa g                                                321

<210> SEQ ID NO 15
<211> LENGTH: 107
<212> TYPE: PRT
<213> ORGANISM: Artificial Sequence
<220> FEATURE:
<223> OTHER INFORMATION: light chain variable region

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Ile Gln Gln Lys Pro Gly Lys Ala Pro Lys Thr Leu Ile
        35                  40                  45

His Arg Ala Asp Arg Leu Ile Asp Gly Val Pro Ser Arg Phe Ser Gly
50                  55                  60

Ser Gly Ser Gly Gln Asp Phe Thr Leu Thr Ile Ser Ser Leu Gln Pro
65                  70                  75                  80

Glu Asp Phe Ala Thr Tyr Tyr Cys Leu Gln Tyr Asp Asp Phe Pro Tyr
                85                  90                  95

Thr Phe Gly Gln Gly Thr Lys Val Glu Ile Lys
                100                 105

<210> SEQ ID NO 16
<211> LENGTH: 449
<212> TYPE: PRT
<213> ORGANISM: Artificial Sequence
<220> FEATURE:
<223> OTHER INFORMATION: heavy chain

<400> SEQUENCE: 16

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

His Ile Asn Trp Val Arg Gln Ala Pro Gly Gln Gly Leu Glu Trp Ile
        35                  40                  45

Gly Tyr Ile Asn Pro Tyr Asn Asp Tyr Ser Arg Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Gly Asn Phe Trp Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 17
<211> LENGTH: 214
<212> TYPE: PRT
<213> ORGANISM: Artificial Sequence
<220> FEATURE:
<223> OTHER INFORMATION: light chain

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Ile Gln Gln Lys Pro Gly Lys Ala Pro Lys Thr Leu Ile
        35                  40                  45

His Arg Ala Asp Arg Leu Ile Asp Gly Val Pro Ser Arg Phe Ser Gly
50                  55                  60

Ser Gly Ser Gly Gln Asp Phe Thr Leu Thr Ile Ser Ser Leu Gln Pro
65                  70                  75                  80

Glu Asp Phe Ala Thr Tyr Tyr Cys Leu Gln Tyr Asp Asp Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 118
<212> TYPE: PRT
<213> ORGANISM: Artificial Sequence
<220> FEATURE:
<223> OTHER INFORMATION: 4-4 humanrized heavy chain variable region

<400> SEQUENCE: 18
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Asn Trp Leu Arg Gln Ala Pro Gly Gln Gly Leu Glu Trp Ile
        35                  40                  45

Gly Trp Ile Tyr Pro Gly Ser Gly Asn Thr Lys Tyr Ser Glu Lys Phe
    50                  55                  60

Lys Asp Arg Ala Thr Leu Thr Val Asp Thr Ser Thr Ser Thr Val Tyr
65                  70                  75                  80

Met Glu Leu Ser Ser Leu Arg Ser Glu Asp Thr Ala Val Tyr Val Cys
                85                  90                  95

Val Arg Asp Gly Tyr Tyr Trp Tyr Phe Asp Val Trp Gly Gln Gly Thr
            100                 105                 110

Leu Val Thr Val Ser Ser
        115

<210> SEQ ID NO 19
<211> LENGTH: 113
<212> TYPE: PRT
<213> ORGANISM: Artificial Sequence
<220> FEATURE:
<223> OTHER INFORMATION: 4-4 humanrized light chain variable region

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Asn
            20                  25                  30

Tyr Asn Gln Lys Asn Tyr Leu Ala Trp Tyr Gln Gln Lys Pro Gly Gln
        35                  40                  45

Pro Pro Lys Leu Leu Val Tyr Phe Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

His Tyr Ser Pro Pro Phe Thr Phe Gly Gln Gly Thr Lys Val Glu Ile
            100                 105                 110

Lys
```